US00PP36306P2

(12) United States Plant Patent
Schulze et al.

(10) Patent No.: US PP36,306 P2
(45) Date of Patent: Dec. 10, 2024

(54) ***HYDRANGEA* PLANT NAMED 'Bailmaceight'**

(50) Latin Name: *Hydrangea macrophylla*
Varietal Denomination: Bailmaceight

(71) Applicant: Bailey Nurseries, Saint Paul, MN (US)

(72) Inventors: Justin Schulze, Athens, GA (US); Oren McBee, Bishop, GA (US); David Jonathan Roberts, Athens, GA (US)

(73) Assignee: BAILEY NURSERIES INC., Saint Paul, MN (US)

( * ) Notice: Subject to any disclaimer, the term of this patent is extended or adjusted under 35 U.S.C. 154(b) by 0 days.

(21) Appl. No.: 18/596,637

(22) Filed: Mar. 6, 2024

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Karen M Redden
*Assistant Examiner* — Zachariah Allan Kay
(74) *Attorney, Agent, or Firm* — Penny J. Aguirre

(57) ABSTRACT

A new cultivar of *Hydrangea macrophylla* plant named 'Bailmaceight' that is characterized by its dark green foliage with red stems, its pure white inflorescences that are not affected by soil pH, and its strong reblooming habit; blooming from summer to until frost.

3 Drawing Sheets

Botanical classification: *Hydrangea macrophylla.*
Varietal denomination: 'Bailmaceight'.

BACKGROUND OF THE INVENTION

The present invention relates to a new and distinct cultivar of *Hydrangea macrophylla* and will be referred to hereafter by its cultivar name, 'Bailmaceight'. 'Bailmaceight' represents a new bigleaf hydrangea, a perennial shrub grown for use in the landscape and as a potted plant.

'Bailmaceight' derived from an ongoing controlled breeding program directed by the Inventors. The goal of the breeding program included developing a new cultivar of *Hydrangea* with a reblooming habit, white inflorescences, dark green foliage, and improved disease resistance and cold tolerance.

'Bailmaceight' arose from a controlled cross made by the Inventors in Watkinsville, Georgia in summer of 2017 between unnamed and unpatented proprietary plants in the Inventor's breeding program; reference no. HM17-W10-02 as the female parent and reference no. HM17-G15-06 as the male parent. The new cultivar was selected as a single unique plant in summer of 2018 from the resulting seedling from the above cross.

Asexual propagation of the new cultivar was first accomplished by softwood stem cuttings under the direction of the Inventors in summer of 2019 in Winterville, Georgia. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailmaceight' as a unique cultivar of *Hydrangea macrophylla.*

1. 'Bailmaceight' exhibits dark green foliage with red stems.
2. 'Bailmaceight' exhibits pure white inflorescences that are not affected by soil pH.
3. 'Bailmaceight' exhibits a strong reblooming habit; blooming from summer to until frost.

The female parent of 'Bailmaceight' differs from 'Bailmaceight' in having less reblooming, a larger plant size, stems that are green in color, and lace-cap type inflorescences. The male parent of 'Bailmaceight' differs from 'Bailmaceight' in having inflorescences that are light pink in color (in absence of aluminum) and a smaller plant size. 'Bailmaceight' can be most closely compared to the *Hydrangea macrophylla* cultivars 'Blushing Bride' (U.S. Plant Pat. No. 17,169) and 'Lanarth White' (not patented). 'Blushing Bride' is similar to 'Bailmaceight' in having white mophead inflorescences and a reblooming habit. 'Blushing Bride' differs from 'Bailmaceight' in having a larger plant size, longer internodes, foliage that is lighter green in color, stems that are green in color, inflorescence colors that are blushed with pink or blue in the presence of aluminum, and less reblooming. 'Lanarth White' is similar to 'Bailmaceight' in having white sterile flowers. Lanarth White' differs from 'Bailmaceight' in having lace-cap type inflorescences, a larger plant size, longer internodes, foliage that is lighter green in color, stems that are green in color, and a non-remontant blooming habit.

BRIEF DESCRIPTION OF THE DRAWINGS

The accompanying color photographs illustrate the overall appearance and distinct characteristics of the new *Hydrangea.* The photographs were taken of a 2-year-old plant as grown in a greenhouse in 2-gallon container in Cottage Grove, Minnesota.

The photograph in FIG. 1 provides a side view of 'Bailmaceight' in bloom.

Figure 1:
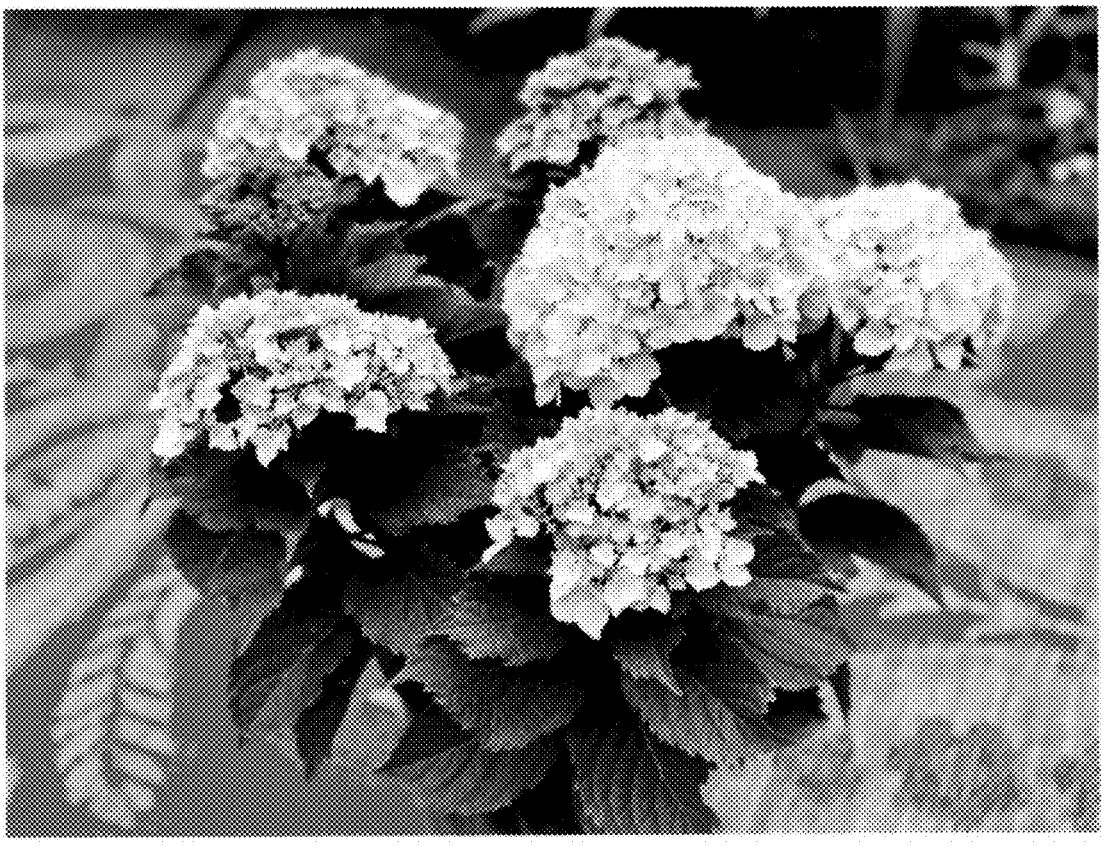
Figure 2:
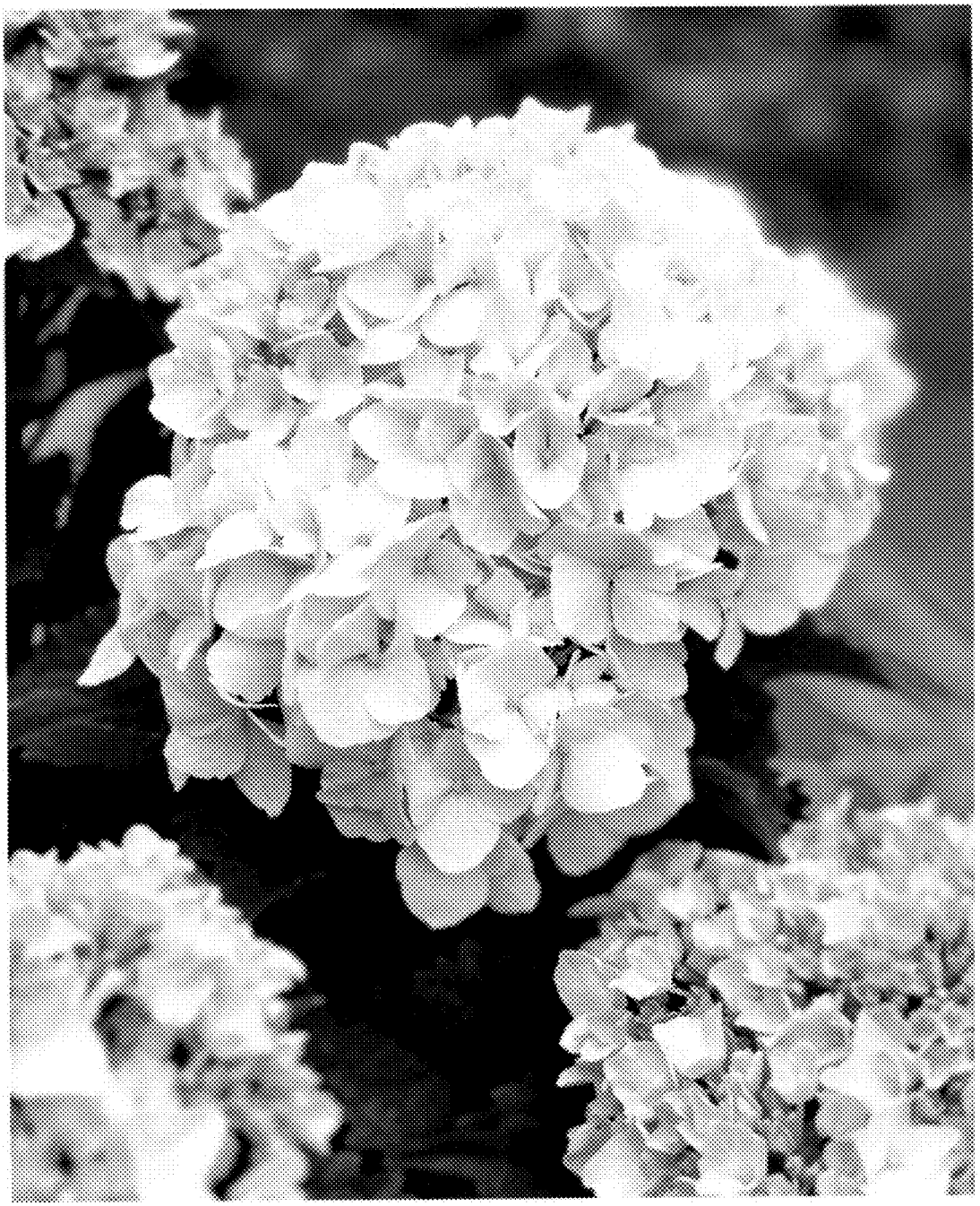

The photograph in FIG. 2 provides a close-up view of a fully open inflorescence of 'Bailmaceight'.

Figure 3:
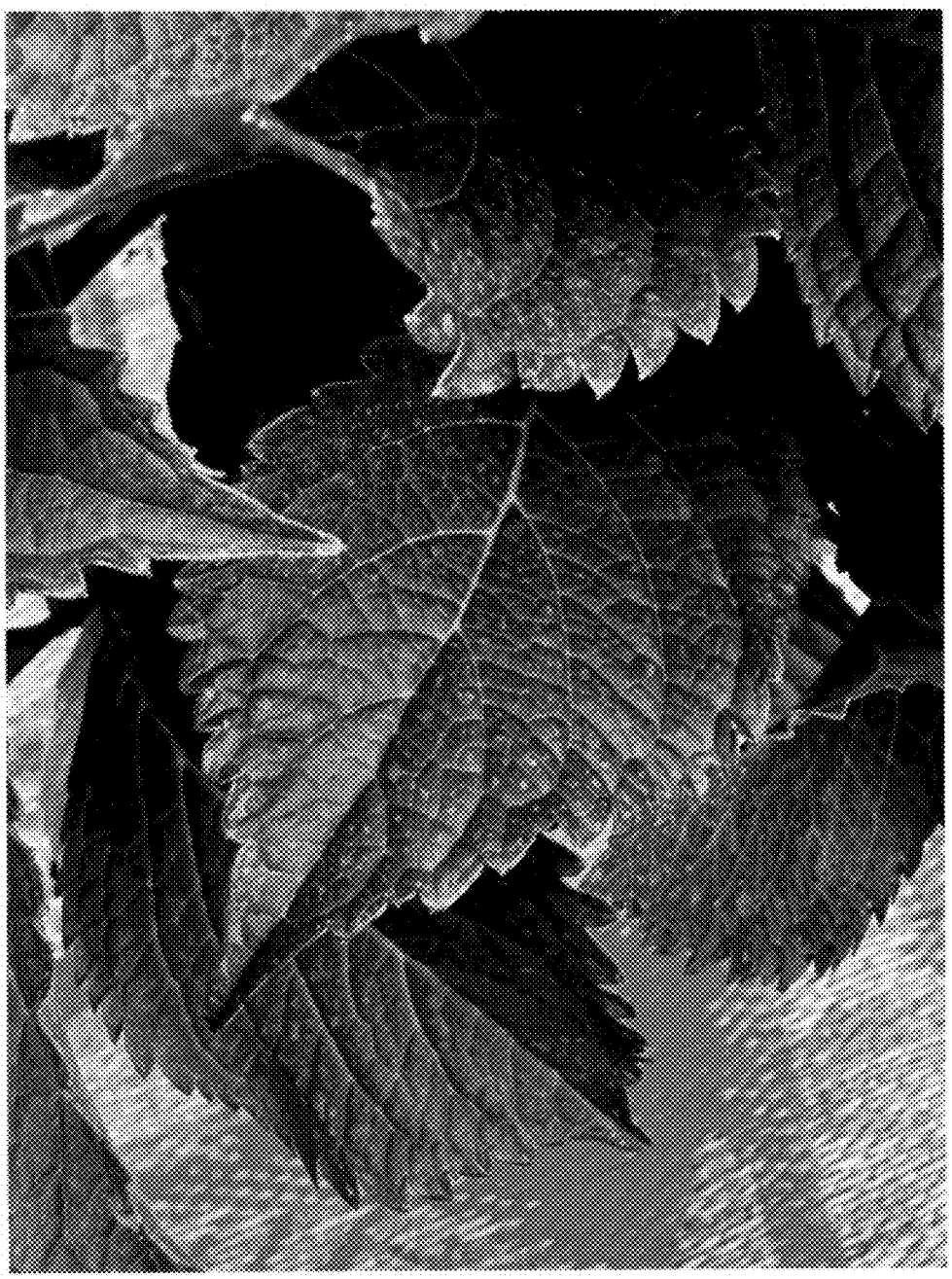

The photograph in FIG. 3 provides a close-up view of the foliage of 'Bailmaceight'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a description of 2-year-old plants of as 'Bailmaceight' as grown outdoors in 2-gallon containers in a greenhouse in Cottage Grove, Minnesota. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—June to frost in Winterville, Georgia.

*Plant type.*—Deciduous shrub, mophead type *Hydrangea.*

*Plant habit.*—Compact, upright, rounded.

*Height and spread.*—41 cm in in height and 50 cm in width as a 2-year-old plant as grown in a container, 0.9 to 1.2 m in height and in width as a fully mature plant in the landscape.

*Hardiness.*—At least in U.S.D.A. Zones 5 to 9.

*Diseases and pests.*—No susceptibility and resistance to diseases or pests has been observed.

*Root description.*—Fine and fibrous, 165A and NN155C in color.

*Propagation.*—Stem cuttings.

*Root development.*—An average of 20 days for root initiation with a young rooted plant produced in an average of 60 days from a rooted cutting.

*Growth rate and vigor.*—Moderate.

Branch description:

*Branch shape.*—Round to slightly flattened oval.

*Branch strength.*—Main and lateral; strong.

*Branch color.*—Young and mature; 144B in color, flushed at the base with 200A, moderately covered in narrow lenticels, 1 mm in length, 202A in color, woody branches; N199A and 200B.

*Branch size.*—Main branches; an average of 5 cm in length, 1.5 cm in diameter (pruned), lateral branches; average of 30 cm in length and 1 cm in diameter.

*Branch surface.*—Young and mature; very glossy, glabrous, older branches; woody, rugose, matte, dry.

*Branch aspect.*—Upright to slightly outward.

*Internode length.*—An average of 1 cm.

*Branching.*—3 main branches, up to 5 lateral branches per main branch.

Foliage description:

*Leaf shape.*—Ovate.

*Leaf arrangement.*—Opposite.

*Leaf division.*—Simple.

*Leaf base.*—Acute.

*Leaf apex.*—Acuminate.

*Leaf margins.*—Serrate.

*Leaf venation.*—Pinnate, upper and lower color 155A, main vein 184A.

*Leaf size.*—Up to 10 cm in length and 7 cm in width.

*Leaf attachment.*—Petiolate.

*Leaf number.*—An average of 20 per lateral stem.

*Leaf surface.*—Young; both surfaces glabrous and rugose, mature lower surface; matte, mature upper surface; leathery with a slight lustrous matte sheen.

*Leaf color.*—Young and mature upper surface; 137A, young and mature lower surface; 138A.

*Petioles.*—An average of 2 cm in length and 3 mm in width, both surfaces are glabrous and glossy, color of both surfaces 185D.

Inflorescence description:

*Inflorescence type.*—Terminal panicle, rounded mophead comprised of a sterile flowers above fertile flowers.

*Lastingness of inflorescence.*—Sterile flowers; persistent for an average of 6 weeks, fertile flowers; self-cleaning, an average of 5 days.

*Inflorescence mumber.*—One per lateral stem.

*Inflorescence size.*—An average of 18 cm in height and 24 cm in diameter.

*Flower number.*—Per mophead; an average of 200 sterile flowers and 50 fertile flowers.

*Flower fragrance.*—None.

*Flower aspect.*—Upright.

*Flower size.*—Sterile flowers; an average of 4 cm in diameter and 1 cm in depth, fertile flowers; an average of 7 mm in diameter and 4 mm in depth.

*Flower type.*—Rotate.

*Peduncles.*—Strong, bendable, oval in shape, an average of 2.5 cm in length and 2 mm in diameter, surface is glossy with a shiny luster, glabrous, color: young; 145C to 145D, randomly flushed with 71A especially around attachments, mature 196C, flushed very randomly with 186A especially around attachments, very sparsely covered in narrow lenticels; 0.8 mm in length, 186A in color.

*Pedicels.*—Sterile flowers; moderately strong, bendable, oval in shape, an average of 2 cm in length and 1.5 mm in diameter, surface is glossy with a shiny luster, glabrous, color; young 157A, mature NN155D, base at attachment flushed with 186A, fertile flowers; moderately strong, bendable, round in shape, an average of 3 cm in length and 1 mm in diameter, surface is glossy with a shiny luster, color; young and mature NN155D.

*Petals.*—Sterile flowers: petal spot (flower bud); 2 mm in depth and diameter, round to oval in shape, color; when young 144B, mature NN155D, when petals open; 4 to 5, an average of 3 mm in length, 2 mm in width, elliptical in shape, cupped, cuneate base, bluntly acute to acute apex, both surfaces velvety, glabrous and matte, thickness is moderate, color; both surfaces NN155D, fertile flowers: petal spot (flower bud); 3.5 mm in diameter and depth, round in shape, color; when young 144A to 144B, mature NN155D, when petals open; 5 to 6, star-shaped en masse, individual petals are elliptical in shape, cupped, 4 mm in length, 2.5 mm in width, acute apex, both surfaces glabrous and matte, thickness is moderate, NN155D, petals drop shortly after opening.

*Sepals*.—Sterile flowers; 4, occasionally 5, rotate and slightly to moderately overlapping, apex slightly emarginate to rounded, base is acute to squared, margins are entire to slightly undulate, deltoid and flattened in shape, an average of 2 cm in length, 3.4 cm in width, both surfaces glabrous, velvety and matte, slight rugose appearance from the veins, medium thickness, color: when opening upper and lower surface; 144C, as it matures turning to a blend of 145C and NN155D, when sepals are fully open upper and lower surface; NN155D, fall color 71B, fertile flowers; 5, fused at base, apex is acute, triangular in shape, an average of 1 mm in length, 0.8 mm in width, both surfaces glabrous, NN155D in color.

Reproductive organs:

*Gynoecium*.—Sterile flowers; 1 pistil, stigma; minute in size average of 0.2 mm, rounded, NN155D in color, style; 0.5 mm in length, NN155D in color, ovary; superior, 1 mm in depth and diameter, round in shape, NN155D in color, fertile flowers; 1 pistil, stigma; tri-fid, 0.4 mm in length, NN155D in color, style; minute, 0.2 mm in length, 157D in color, ovary; superior, round in shape, 1.2 mm in depth, 1 mm in diameter, NN155D in color.

*Androecium*.—Sterile flowers: an average of 5 stamens, filaments; an average of 2 mm in length, 0.4 mm in diameter, NN155D in color, anthers; round in shape, an average of 1 mm in diameter, NN155D in color, fading to 164A, pollen; not observed at the time of data collection, fertile flowers: an average of 6 stamens, filaments; an average of 3 mm in length, 0.3 mm in diameter, and NN155D in color, anthers; square to round in shape, bifid, an average of 1 mm in width and depth, NN155D in color, pollen; not observed at the time of data collection.

*Fruit and seed*.—None observed to date.

It is claimed:

1. A new and distinct cultivar of *Hydrangea* plant named 'Bailmaceight' substantially as herein illustrated and described.

* * * * *